United States Patent
Kandula

(10) Patent No.: US 11,648,240 B2
(45) Date of Patent: May 16, 2023

(54) PHARMACEUTICAL COMPOSITION COMPRISING FAMOTIDINE, LIDOCAINE AND MELATONIN

(71) Applicant: Cellix Bio Private Limited, Hyderabad (IN)

(72) Inventor: Mahesh Kandula, Andhra Pradesh (IN)

( * ) Notice: Subject to any disclaimer, the term of this patent is extended or adjusted under 35 U.S.C. 154(b) by 0 days.

(21) Appl. No.: 17/488,238

(22) Filed: Sep. 28, 2021

(65) Prior Publication Data

US 2022/0233508 A1 Jul. 28, 2022

Related U.S. Application Data

(63) Continuation of application No. PCT/IB2021/057999, filed on Sep. 2, 2021.

(30) Foreign Application Priority Data

| Jan. 23, 2021 | (IN) | 202141003284 |
| Feb. 17, 2021 | (IN) | 202141006680 |
| Apr. 8, 2021 | (IN) | 202141016620 |

(51) Int. Cl.
| *A61K 31/426* | (2006.01) |
| *A61K 31/167* | (2006.01) |
| *A61K 9/20* | (2006.01) |
| *A61K 9/00* | (2006.01) |
| *A61K 31/4045* | (2006.01) |

(52) U.S. Cl.
CPC .......... *A61K 31/426* (2013.01); *A61K 9/0056* (2013.01); *A61K 9/20* (2013.01); *A61K 31/167* (2013.01); *A61K 31/4045* (2013.01)

(58) Field of Classification Search
CPC ................ A61K 31/426; A61K 31/167; A61K 31/4045; A61K 9/0056; A61K 9/20
See application file for complete search history.

(56) References Cited

U.S. PATENT DOCUMENTS

| 2003/0175360 A1 | 9/2003 | Luzzatti |
| 2020/0345767 A1 | 11/2020 | Geibel et al. |

FOREIGN PATENT DOCUMENTS

| CN | 1814291 A | 8/2006 |
| CN | 103301122 A | 9/2013 |
| EP | 2182947 B1 | 9/2019 |
| WO | WO2015153552 A1 | 10/2015 |

OTHER PUBLICATIONS

Baykara B, Tekmen I, Pekcetin C, Ulukus C, Tuncel P, Sagol O, Ormen M, Ozogul C. The protective effects of carnosine and melatonin in ischemia-reperfusion injury in the rat liver. Acta Histochem. 2009;111(1):42-51. doi:10.1016/j.acthis.2008.03.002. Epub Jun. 12, 2008. PMID: 18554692.

Kishikawa, K., Namiki, A., Miyashita, K. and Saitoh, K. (1990), Effects of famotidine and cimetidine on plasma levels of epidurally administered lignocaine. Anaesthesia, 45: 719-721. https://doi.org/10.1111/j.1365-2044.1990.tb14437.x.

Karabulut-Bulan, O., Us, H., Bayrak, B.B. et al. The role of melatonin and carnosine in prevention of oxidative intestinal injury induced by gamma irradiation in rats. Biologia 72, 935-945 (2017). https://doi.org/10.1515/biolog-2017-0092.

GNHIndia.com. Orabliss Oral Gel—Lidocaine (2% W/W), Zinc Carnosine (2% W/W). Accessed on Mar. 11, 2021: 7 pages, https://www.gnhindia.com/products/orabliss-oral-gel-lidocaine2-w-w-zinc-carnosine2-w-w/.

Prescribers' Digital Reference. Lidocaine Hydrochloride—Drug Summary. Dec. 2, 2015:2 pages. https://www.pdr.net/drug-summary/4-Xylocaine-MPF-lidocaine-hydrochloride-2023.

Prescribers' Digital Reference. Lidocaine Hydrochloride—Drug Summary. May 9, 2017: 29 pages. https://www.pdr.net/drug-summary/4--Xylocaine-MPF-lidocaine-hydrochloride-2023.

Prescribers' Digital Reference. Lidocaine Hydrochloride—Drug Summary. Sep. 17, 2020: 35 pages. https://www.pdr.net/drug-summary/4--Xylocaine-MPF-lidocaine-hydrochloride-2023.

*Primary Examiner* — James D. Anderson
(74) *Attorney, Agent, or Firm* — S. Elizabeth Miller, Esq.

(57) ABSTRACT

The present disclosure provides a pharmaceutical composition comprising Famotidine or salt or hydrates or solvates thereof, Lidocaine or salt or hydrates or solvates thereof, and Melatonin or salt or hydrates or solvates thereof. The compositions of the present disclosure may find utility in treatment of oral mucositis, gastritis, gastric ulcers and the like conditions. Aspects of the present disclosure also relates to method of treating oral and gastrointestinal diseases/conditions using the advantageous compositions of the present disclosure.

14 Claims, No Drawings

PHARMACEUTICAL COMPOSITION COMPRISING FAMOTIDINE, LIDOCAINE AND MELATONIN

PRIORITY

The present application is a continuation of International Patent Application No. PCT/2021/057999, which was filed Sep. 2, 2021, which claims benefit of the Indian provisional Application No. 202141003284 filed on Jan. 23, 2021, Indian provisional Application No. 202141006680 filed on Feb. 17, 2021, and Indian provisional Application No. 202141016620 filed Apr. 8, 2021, the entire disclosures of which are relied on for all purposes and are incorporated into this application by reference.

TECHNICAL FIELD

The present disclosure generally relates to the field of pharmaceutical compositions. In particular, the present disclosure provides a pharmaceutical composition comprising Famotidine or salt or hydrates or solvates thereof, Lidocaine or salt or hydrates or solvates thereof, and Melatonin or salt or hydrates or solvates thereof. The compositions of the present disclosure may find utility in treatment of oral mucositis, gastritis, gastric ulcers and the like conditions.

BACKGROUND

Inflammation is a biological response of the immune system that can be triggered by various infectious, immunological, physical, chemical, and inert agents. These factors may induce inflammatory responses in the lung, skin, heart, pancreas, liver, kidney, brain, intestinal tract and reproductive system, potentially leading to tissue damage or disease. Classical signs of inflammation include redness; swelling; heat; and pain. Depending upon the defense capacity of the host and duration of response, inflammation can be classified as acute and chronic. Inflammation often involves a series of vascular and cellular events. Although inflammatory response processes depend on the precise nature of the initial stimulus and its location in the body, they all share a common mechanism, which can be summarized as follows: 1) cell surface pattern receptors recognize detrimental stimuli; 2) inflammatory pathways are activated; 3) inflammatory markers are released; and 4) inflammatory cells are recruited. An inflammatory mediator is a chemical messenger that acts on blood vessels and or cells to promote an inflammatory pathway. The chemical mediators like histamine, Serotonin, prostaglandins, leukotrienes, cytokines, free radicals, oxygen, and arachidonic acid metabolites are released on initiation of tissue injury by degranulation of various immune cells like mast cells, eosinophils, basophils, platelets, lymphocytes etc.

Pain is a warning signal, primarily protective in nature, but causes discomfort and suffering, may even be unbearable and incapacitating. It is the most important symptom caused by C, A-S afferent fibers activation during tissue injury and inflammation. Histamine, serotonin, ROS, prostanoids, kinins are major inflammatory mediators involved in causing nociceptive and neuropathic pain.

The chronic active inflammation is dominated by neutrophils, macrophages, lymphocytes and plasma cells. Several interleukins (IL-8, IL-10 and IFN-γ) are involved in the inflammatory process in the gastric mucosa. CD4 and CD19 were significantly increased in patients with increased gastric inflammation. The mediators that coordinate inflammatory responses also have the capability to alter the resistance of the mucosa to injury induced by noxious/irritant substances, while others render the mucosa more susceptible to injury. The inflammatory mediators that modulate GI mucosal defense are nitric oxide, the eicosanoids (prostaglandins, leukotrienes, and thromboxanes), neuropeptides, cytokines, and proteinases. Many of these mediators are considered potential therapeutic targets for the treatment of ulcerative diseases of the digestive tract. Inflammation of GI tract can cause ulcer, inflamed mucosal layers, bleeding. The GI tract disorder can be drug induced, pathogen induced or others. In such cases conditions can be treated by avoiding the drug and using gastric acid secretion inhibitors such as proton pump inhibitor, 112 anti-histaminic, anti-cholinergics and prostaglandin analogues are helpful. Long time use of acid blocker or acid reducing agents affects the functions associated with hydrochloric acid in the digestion. Famotidine, a histamine-2 receptor antagonist suppresses gastric acid production. In-vitro studies have indicated that famotidine inhibits human immunodeficiency virus replication and also sars-cov-2.

Mucositis is the painful inflammation and ulceration of the mucous membranes lining the digestive tract, usually as an adverse effect of chemotherapy and radiotherapy treatment for cancer. Mucositis can occur anywhere along the gastrointestinal (GI) tract, but oral mucositis refers to the particular inflammation and ulceration that occurs in the mouth. Oral mucositis is a common and often debilitating complication of cancer treatment.

Current treatment options available for such oral and gastrointestinal disorders/conditions, in particular, for oral mucositis include non-pharmacological oral hygiene care, decontamination and pharmacological agents for example, systemic analgesics, topical palliative agents, Oral Rinses like 2% viscous lidocaine solution, magic mouthwash preparations, a topical morphine solution are used to control pain but still there need of effective pain management and there is no statistical significant evidence to suggest that available mouthwashes are effective in pain relief (based on VAS score) and opioid, anesthetic agents are associated with severe side effects like mouth dryness, loss of taste, dizziness, stomach discomfort and constipation and they are short lasting.

To solve the above problems, particularly, the microbial infection and oxidative stress conditions associated with oral and gastrointestinal disorders/conditions, significant efforts have been put forth by the researchers to find products for treating oral and gastrointestinal disorders. However, none of the existing approaches seem to satisfy the existing needs. A need is also felt of improved formulations that are easy to administer and aids in improving patient compliance. The present disclosure satisfies the existing needs, at least in part, and overcomes one or more disadvantages of the conventional approaches.

OBJECTS

One of the objects of the present disclosure is to provide a pharmaceutical composition that may overcome the limitations associated with the conventional compositions.

Another object of the present disclosure is to provide a composition that exhibits superior storage stability and functional reciprocity.

Further object of the present disclosure is to provide a composition that is easy to prepare and is economical.

Yet another object of the present disclosure is to provide a pharmaceutical composition to deliver as an immediate release or modify or control the delivery rate of different active agents in the formulation.

Still another object of the present disclosure is to deliver the active agents either simultaneously or concurrently or concomitantly to a subject for treatment of a disease.

SUMMARY

The present disclosure generally relates to the field of pharmaceutical compositions. In particular, the present disclosure provides a pharmaceutical composition comprising Famotidine or salt or hydrates or solvates thereof, Lidocaine or salt or hydrates or solvates thereof, and Melatonin or salt or hydrates or solvates thereof.

In an embodiment, the composition comprises Famotidine or salt or hydrates or solvates thereof, Lidocaine or salt or hydrates or solvates thereof and Melatonin or salt or hydrates or solvates thereof in a weight ratio ranging from 1:1:1 to 100:400:1. In an embodiment, the composition is a fixed dose combination.

In an embodiment, the composition comprises Famotidine or salt or hydrates or solvates thereof, Lidocaine or salt or hydrates or solvates thereof and Melatonin or salt or hydrates or solvates thereof in a weight ratio ranging from 2:5:1 to 10:50:1.

In an embodiment, Famotidine or salt or hydrates or solvates thereof is present in an amount ranging from 10 mg to 100 mg. In embodiment, Lidocaine or salt or hydrates or solvates thereof is present in an amount ranging from 50 mg to 400 mg. In an embodiment, Melatonin or salt or hydrates or solvates thereof is present in an amount ranging from 1 mg to 60 mg.

In an embodiment, the composition includes Famotidine or salt or hydrates or solvates thereof is present in an amount ranging from 10 mg to 100 mg, Lidocaine or salt or hydrates or solvates thereof is present in an amount ranging from 50 mg to 400 mg, and Melatonin or salt or hydrates or solvates thereof is present in an amount ranging from 1 mg to 60 mg. In one embodiment, Lidocaine is present as hydrochloride monohydrate.

The composition also includes a pharmaceutically acceptable excipient. The pharmaceutically acceptable excipient is selected from any or a combination of: a diluent, an antioxidant, a preservative, an alkalizing agent, a buffering agent, a disintegrant, a binder, an anti-foaming agent, a solvent, a glidant, a lubricant, a flavoring agent, a coating agent, a rate controlling polymer or non-polymer, a zinc salt, a fatty acid or derivative thereof, an amino acid or metabolites or amino acid derivatives, a bulking agent, an anti-tacking agent, an emulsifier, a surfactant, a plasticizer and a stabilizer.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof. In an embodiment, the composition comprises an intra-granular portion and an extra-granular portion, wherein the intra-granular portion comprises Famotidine or salt or hydrates or solvates thereof, Lidocaine or salt or hydrates or solvates thereof, Melatonin or salt or hydrates or solvates thereof and a pharmaceutically acceptable excipient, and the extra-granular portion comprises a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, wherein the intra-granular portion comprises Lidocaine or salt or hydrates or solvates thereof, Melatonin or salt or hydrates or solvates thereof and a pharmaceutically acceptable excipient, and the extra-granular portion comprises Famotidine or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, wherein the intra-granular portion comprises Famotidine or salt or hydrates or solvates thereof, Melatonin or salt or hydrates or solvates thereof and a pharmaceutically acceptable excipient, and the extra-granular portion comprises Lidocaine or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, wherein the intra-granular portion comprises Famotidine or salt or hydrates or solvates thereof and Lidocaine or salt or hydrates or solvates thereof and a pharmaceutically acceptable excipient, and the extra-granular portion comprises Melatonin or salt or hydrates or solvates thereof and a pharmaceutically acceptable excipient.

In yet another embodiment, the composition comprises an intra-granular portion and an extra-granular portion, wherein the intra-granular portion comprises Famotidine in an amount of 40 mg, Lidocaine hydrochloride monohydrate in an amount of 100 mg, Melatonin in an amount of 10 mg, and a pharmaceutically acceptable excipient, and the extra-granular portion comprises a pharmaceutically acceptable excipient.

In an embodiment, the portions are compressed together to obtain any of: a tablet dosage form and a lozenge dosage form, optionally coated with a seal coat. In an embodiment, the seal coat is an aqueous seal coat.

DETAILED DESCRIPTION

The present disclosure generally relates to the field of pharmaceutical compositions.

As used herein, the following terms and phrases shall have the meanings set forth below. Unless defined otherwise, all technical and scientific terms used herein have the same meaning as commonly understood to one of ordinary skill in the art. It is also understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "an active agent" or "an active ingredient" refers not only to a single active agent but also to a combination of two or more different active agents, "a dosage form" refers to a combination of dosage forms as well as to a single dosage form, and the like.

The term "active agent" or "therapeutic agent", encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The term "combination therapy" or "combined treatment" or "in combination" as used herein denotes any form of concurrent or concomitantly or co-administration of active agents for treating inflammation, inflammation mediated pain, ulcers, ulcer mediated pain, oral and gastrointestinal diseases.

The terms "treating" and "treatment" as used herein refers to reduction in severity and/or frequency of symptoms, elimination of symptoms and/or underlying cause, and improvement or remediation of damage caused thereby. Thus, "treating" a subject/patient as described herein encompasses treating oral, gastrointestinal and esophageal diseases. The ulcers and gastrointestinal disease as disclosed herein includes peptic ulcers that are chronic lesion or painful sores or seen on the lining of gastrointestinal tracts due to aggressive action of gastric-peptic juices. Peptic ulcer in the stomach is called a gastric ulcer and in the duodenum is called duodenal ulcer. The ulcers are caused because of imbalance between defensive mechanism of gastric mucosa (epithelial cells lining, secretion of bicarbonate and mucus), and aggressive factors (use of NSAIDs, corticosteroids, *H. pylori* infection, secretion of pepsin, gastric acid, smoking, alcohol). Gastroesophageal reflux disease (GERD) or peptic esophagitis or reflux esophagitis a clinical condition in which the reflux of stomach acid into the esophagus impacts a subject's normal functioning or to cause damage to the esophagus, gastritis, odynophagia, or painful swallowing, and dysphagia, regurgitation of food, belching, nausea, vomiting and sore throat. Further gastric esophagitis and related diseases such as radiation induced esophagitis, esophageal tumor, gastro-intestinal symptoms, chronic pharyngitis, inflammation mediated pain, ulcers mediated pain, Barrett's esophagus, esophageal adenocarcinoma, GERD-related pulmonary symptoms, oral, gastrointestinal diseases, inflammation, allergy, gastric cancer, neoplasm mediated secretions, esophagus related neoplasm, oral inflammation, head and neck cancer related oral and gastrointestinal complications, covid-19, cytokine storms, effectively in short time. Furthermore, oral and gastrointestinal diseases including oral mucositis, oral ulcers, dry mouth, peptic ulcers, gastric ulcer, duodenal ulcer, esophageal ulcers, gastroesophageal reflux disease (GERD), inflammation, allergy, stomatitis, insomnia, gastric cancer, Covid-19, cytokine mediated inflammation, severe erosive esophagitis, pressure ulcers, their associated symptoms and Zollinger Ellison syndrome. The Barrett's esophagus is a serious complication of chronic GERD in which the epithelium of the esophagus is replaced with abnormal tissue. Barrett's esophagus is a risk factor for the development of cancer of the esophagus. Zollinger-Ellison syndrome is a rare condition in which one or more tumors form in the pancreas or the upper part of the small intestine (duodenum). These tumors, called gastrinomas, secrete large amounts of the hormone gastrin, which causes the stomach to produce too much acid. Mucositis is the painful inflammation and ulceration of the mucous membranes lining the digestive tract, usually as an adverse effect of chemotherapy and radiotherapy treatment for cancer. Mucositis can occur anywhere along the gastrointestinal (GI) tract, but oral mucositis refers to the particular inflammation and ulceration that occurs in the mouth. Oral mucositis is a common and often debilitating complication of cancer treatment. Use in treating ulcers in subjects with human immunodeficiency virus (HIV) infection and sars-cov-2 infection. HIV patients suffer from persistent, painful ulcers seen on the soft palate, buccal mucosa, tonsillar area or tongue, which are referred to as aphthous ulcers.

The term "dosage form" denotes any form of a pharmaceutical composition that contains an amount of active agent sufficient to elicit a desired therapeutic response.

The term "controlled release" refers to a drug-containing formulation or fraction thereof in which release of the drug is not immediate. The term "controlled release" as used herein includes sustained release, non-immediate release and delayed release formulations.

The term "sustained release" (synonymous with "extended release") is used in its conventional sense to refer to a drug formulation that provides for gradual release of a drug over an extended period of time.

The term "pharmaceutically acceptable" means the material incorporated into a pharmaceutical composition that can be administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"Pharmacologically active" (or simply "active") as in a pharmacologically active derivative or analog, refers to a derivative or analog having the same type of pharmacological activity as the parent compound and approximately equivalent in degree.

The present disclosure provides a pharmaceutical composition comprising: Famotidine or salt or hydrates or solvates thereof, Lidocaine or salt or hydrates or solvates thereof, and Melatonin or salt or hydrates or solvates thereof. In an embodiment, the composition is a fixed dose combination. The compositions of the present disclosure may find utility in treatment of oral mucositis, gastritis, gastric ulcers and the like conditions.

In an embodiment, the composition comprises Famotidine or salt or hydrates or solvates thereof, Lidocaine or salt or hydrates or solvates thereof and Melatonin or salt or hydrates or solvates thereof in a weight ratio ranging from 1:1:1 to 100:400:1.

In an embodiment, the composition comprises Famotidine or salt or hydrates or solvates thereof, Lidocaine or salt or hydrates or solvates thereof and Melatonin or salt or hydrates or solvates thereof in a weight ratio ranging from 1:1:1 to 10:50:1.

In an embodiment, the composition comprises Famotidine or salt or hydrates or solvates thereof, Lidocaine or salt or hydrates or solvates thereof and Melatonin or salt or hydrates or solvates thereof in a weight ratio ranging from 2:5:1 to 10:50:1.

In an embodiment, the composition comprises Famotidine or salt or hydrates or solvates thereof, Lidocaine or salt or hydrates or solvates thereof and Melatonin or salt or hydrates or solvates thereof in a weight ratio ranging from 3:7:1 to 8:40:1.

In an embodiment, the composition comprises Famotidine or salt or hydrates or solvates thereof, Lidocaine or salt or hydrates or solvates thereof, and Melatonin or salt or hydrates or solvates thereof in a weight ratio of 4:10:1.

In an embodiment, Famotidine or salt or hydrates or solvates thereof is present in the composition in an amount ranging from 10 mg to 100 mg. In embodiment, Lidocaine or salt or hydrates or solvates thereof is present in an amount ranging from 50 mg to 400 mg. In an embodiment, Melatonin or salt or hydrates or solvates thereof is present in an amount ranging from 1 mg to 60 mg.

In an embodiment, Famotidine or salt or hydrates or solvates thereof is present in the composition in an amount of 10 mg to 100 mg. Alternatively, Famotidine or salt or hydrates or solvates thereof is present in an amount of 20 mg to 60 mg. Still alternatively, Famotidine or salt or hydrates or solvates thereof is present in an amount of 30 mg to 50 mg. In an embodiment, the amount of Famotidine or salt or hydrates or solvates thereof in the composition is 40 mg.

In an embodiment, Lidocaine or salt or hydrates or solvates thereof is present in the composition in an amount of 50 mg to 400 mg. Alternatively, Lidocaine or salt or hydrates or solvates thereof is present in an amount of 60 mg to 250 mg. Alternatively, Lidocaine or salt or hydrates or solvates thereof is present in an amount of 70 mg to 130 mg. Still alternatively, Lidocaine or salt or hydrates or solvates thereof is present in an amount of 90 mg to 110 mg. In an embodiment, the amount of Lidocaine or salt or hydrates or solvates thereof in the composition is 100 mg. In an embodiment, Lidocaine is present as Lidocaine hydrochloride monohydrate.

The composition includes Melatonin or salt or hydrates or solvates thereof in an amount ranging from 1 mg to 60 mg. Alternatively, Melatonin or salt or hydrates or solvates thereof is present in an amount of 3 mg to 40 mg. Alternatively, Melatonin or salt or hydrates or solvates thereof is present in an amount of 5 mg to 15 mg. Still alternatively, Melatonin or salt or hydrates or solvates thereof is present in an amount of 8 mg to 12 mg. In an embodiment, the amount of Melatonin or salt or hydrates or solvates thereof in the composition is 10 mg.

In an embodiment, any of the three active agents famotidine, melatonin and lidocaine are given simultaneously as individual formulations/compositions. In another embodiment, two active agents of the three active agents famotidine, melatonin and lidocaine are given as a formulation/composition and the remainder of the active agent is given simultaneously as a separate formulation/composition to a subject.

In an embodiment, famotidine, lidocaine, melatonin are given simultaneously as individual formulations/compositions. In an embodiment, famotidine and lidocaine are given in a combination as a composition/formulation and melatonin is given simultaneously as a separate composition/formulation to a subject. Alternatively, lidocaine and melatonin are given in a combination as a composition/formulation and famotidine is given simultaneously as a separate composition/formulation to a subject. Alternatively, famotidine and melatonin are given in a combination as a composition/formulation and lidocaine is given simultaneously as a separate composition/formulation to a subject.

In another embodiment, active agents famotidine, lidocaine and melatonin are formulated as individual formulations/compositions in titrated strengths or binary mixture compositions or a fixed dosage combination of either 2 active agents selected and 1 active agent given simultaneously for the treatment of a disease/condition in a subject.

In an embodiment, any of the three active agents famotidine, melatonin and lidocaine are given simultaneously as individual formulations/compositions or two active agents are given in a combination and one active agent is given concomitantly along with the two active agents in combination to a subject.

In another embodiment, famotidine, lidocaine and melatonin are given concomitantly as individual formulations/compositions or famotidine and lidocaine are given in a combination and melatonin is given concomitantly as a separate formulation or lidocaine and melatonin are given in a combination and famotidine is given concomitantly as a separate formulation or famotidine and melatonin are given in a combination and lidocaine is given concomitantly as a separate formulation to a subject.

In another embodiment, active agents famotidine, lidocaine and melatonin are formulated as individual formulations/compositions in titrated strengths or binary mixture compositions or as fixed dosage combination of either 2 active agents and 1 active agent given concomitantly for the treatment of a disease/condition in a subject.

In another embodiment, active agents famotidine, lidocaine and melatonin are formulated as individual formulations/compositions in titrated strengths or binary mixture compositions or as a fixed dosage combination of either 2 active agents selected and 1 active agent is given concomitantly for the treatment of a disease/condition in a subject.

The composition also includes a pharmaceutically acceptable excipient. The pharmaceutically acceptable excipient may be selected from any or a combination of: a diluent, an anti-oxidant, a preservative, an alkalizing agent, a buffering agent, a disintegrant, a binder, an anti-foaming agent, a solvent, a glidant, a lubricant, a flavoring agent, a sweetener, a coating agent, a rate controlling polymer or non-polymer, a zinc salt, a fatty acid or derivative thereof, an amino acid or metabolites or amino acid derivatives, a bulking agent, an anti-tacking agent, an emulsifier, a surfactant, a plasticizer and a stabilizer.

In an embodiment, the diluent(s) include(s), but not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, and magnesium aluminum silicate and mixtures thereof.

In an embodiment, the anti-oxidant(s) and preservative(s) include(s), but not limited to, L-Carnosine, vitamin A, vitamin E, vitamin C, retinyl palmitate, and selenium, citric acid, sodium citrate, methyl paraben, propyl paraben, p-hydroxybenzoic acid esters, sorbic acid, benzoic acid, propionic acid or salts thereof; Alcohols such as benzyl alcohol, butanol or ethanol, isopropyl alcohol, and quaternary ammonium compounds such as benzalkonium chloride, sodium benzoate and mixtures thereof.

In an embodiment, the alkalizing agent(s) include(s), but not limited to, ammonia solution NF, Ammonium Carbonate NF, Diethanolamine NF, monoethanolamine, Potassium Hydroxide NF, Sodium Bicarbonate USP, Sodium Borate NF, Sodium Carbonate NF, Sodium Hydroxide NF, sodium Phosphate Dibasic USP, trolamine NF, calcium carbonate, magnesium carbonate, magnesium oxide, magnesium hydroxide, magnesium trisilicate, aluminum hydroxide, aluminum carbonate, magnesium aluminium silicate hydrate, potassium bicarbonate, sodium bicarbonate, sodium citrate, potassium citrate, aluminum sulfate, calcium carbonate and mixtures thereof.

In an embodiment, the buffering agent(s) include(s), but not limited to, a bicarbonate salt of alkali earth metal, amino acids, an acid salt of an amino acid, an alkali salt of an amino acid and mixture thereof.

In an embodiment, the disintegrant(s) include(s), but not limited to Croscarmellose sodium, microcrystalline cellulose, low-substituted hydroxypropyl cellulose, alginic acid and alginates, modified starches, sodium starch glycolate, sodium carboxy methyl cellulose, carboxymethyl cellulose calcium, polyvinylpyrrolidone, docusate sodium, guar gum and mixtures thereof.

In an embodiment the binder(s) include(s), but not limited to, hypromellose (or hypromellose 5 cps), polyvinyl pyrrolidone, copolymers of vinyl pyrrolidone with other vinyl derivatives, hydroxypropyl cellulosic derivatives (such as methylcellulose, carboxymethyl cellulose, hydroxyethyl cellulose, hydroxyethylmethyl cellulose, hydroxypropylcellulose etc.), polyacrylates (such as Carbopol, polycarbophil, etc), Povidone (all grades), Polyox of any molecular weight or grade, irradiated or not, maize starch, povidone, copovidone, corn starch, starch, polyvinylpyrrolidone (PVP), microcrystalline cellulose, powdered acacia, gelatin, guar gum, carbomer such as carbopol, polymethacrylates, starch and mixtures thereof.

In an embodiment the anti-foaming agent(s) include(s), but not limited to, alcohols such as cetostearyl alcohol, insoluble oils such as castor oil, stearates, polydimethylsiloxanes and other silicones derivatives, ethers, paraffin oil, paraffin wax, glycols, simethicone (or simethicone 30% emulsion) and mixtures thereof.

In an embodiment, solvent(s) include(s), but not limited to, methanol, ethanol, n-propanol, isopropanol, hexane, heptane, petroleum ether, cyclohexane, diethyl ether, diisopropyl ether, ethyl acetate, methyl acetate, ethyl formate, methyl formate, isobutyl acetate, n-butyl acetate, methylene chloride, ethylene chloride, chloroform, carbon tetrachloride, acetone, ethyl methyl ketone, diisobutyl ketone, methyl isobutyl ketone, 1,4-dioxane, toluene, ammonia solution, glacial acetic acid, ammonium hydroxide, sodium hydroxide, calcium hydroxide, calcium carbonate, potassium hydroxide, potassium carbonate, water and mixtures thereof.

In an embodiment, the glidant(s) include(s), but are not limited to, colloidal silicon dioxide, stearic acid, talk, aluminum silicate and mixtures thereof.

In an embodiment, the lubricant(s) include(s), but not limited to, stearic acid, magnesium stearate, sodium stearyl fumarate, sodium lauryl sulphate, magnesium lauryl sulphate, fumaric acid, glyceryl palmitostearate, zinc stearate, calcium stearate, silica, talc, polyethylene glycol, paraffin and mixtures thereof.

In an embodiment, the flavoring agent(s) include(s), but not limited, cherry, maple, pineapple, orange, raspberry, banana-vanilla, peppermint, butterscotch, strawberry, vanilla, apricot, cinnamon, honey, lime, peach-orange, peach-rum, raspberry, wild cherry, mint and mixtures thereof.

In an embodiment, coating agent(s) include(s), but not limited to Cellulosics, such as hydroxypropyl methyl cellulose (HPMC), methyethylcellulose (MEC), carboxymethyl celluolose (CMC), carboxymethyl ethylcelluolose (CMEC), hydroxyethyl cellulose (HEC), Hydroxypropyl cellulose (IIPC), cellulose acetate phthalate (CAP), hydroxypropyl methyl cellulose phthalate (HPMCP), hydroxypropyl methyl cellulose acetate succinate (HPMCAS), hypromellose, povidone, copovidone, and ethyl cellulose (EC); Vinyls, such as polyvinyl alcohol; Acrylics, such as methacrylic acid/ethylacrylate copolymers (often used for enteric or delayed release coatings), Natural derivatives, such as shellac or alginate and mixtures thereof.

In an embodiment, the rate controlling polymer(s) include(s), but not limited to, cellulose acetate, alkyl celluloses, hydroxyalkyl, acrylic polymers, copolymers, dialkylphthalates, dibutyl phthalate, microcrystalline wax and mixtures thereof.

In an embodiment, the rate controlling non-polymer(s) include(s), but not limited to fat, wax, fatty acid, fatty acid ester, long chain monohydric alcohol or their ester and mixtures thereof.

In an embodiment, zinc salt(s) include(s), but not limited to, zinc oxide, zinc stearate, zinc L-carnosine, zinc acetate, zinc chloride, zinc bromide, zinc fluoride, zinc hexafluorosilicate, zinc iodide, zinc molybdate, zinc nitrate, zinc molybdite, zinc oxalate, zinc perchlorate, zinc tetrafluoroborate, zinc sulfate and mixtures thereof.

In an embodiment, the fatty acid(s) or derivatives thereof include(s), but not limited to, fatty acids with C1 to C30 carbons, which includes long chain fatty acids; saturated or unsaturated fatty acids and derivatives thereof (monounsaturated fatty acids (MUFAs) C18:1n-12c, C16:1n-5, C16:4n-1 and the polyunsaturated fatty acids (PUFAs) C16:3n-4, C20:3n-3, C20:4n-6, C21:5n-3 and C18:2n-9c,12t); hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; dicaprylate; laurate, monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty acid derivatives such as diglyceryl lauryl fumarate (DGLF), diglyceryl lauryl succinate, diglyceryl capryl succinate, diglyceryl capryl fumarate; fatty alcohols associated with polyethoxylate fatty alcohols; cetyl alcohol; octyldodecanol; myristyl alcohol; isopropyl myristate, isopropyl palmitate, stearic acid, lauric acid, EPA, DHA, linoleic acid, linolenic acid, stearyl alcohol and mixture thereof. In an embodiment, diglyceryl lauryl fumarate (DGLF), diglyceryl lauryl succinate, diglyceryl capryl succinate or diglyceryl capryl fumarate are used in the composition to either delay disintegration and/or absorption and thereby provide sustained action over a longer period.

In an embodiment, the amino acids or metabolites or amino acid derivatives include(s), but not limited to, glycine, glutamine, asparagine, arginine, lysine in biologically active enantiomeric forms, L-carnosine, L-carnitine, choline, betaine, taurine, glycosaminoglycans including hyaluronic acid, chondroitin sulfate, glucosamine, L-glucosamine, heparins and mixtures thereof.

In an embodiment, the bulking agent(s) include(s), but not limited to, lactose USP, Starch 1500, mannitol, erythritol, sorbitol, maltodextrin, malitol or other non-reducing sugars; microcrystalline cellulose (e.g., Avicel), dibasic calcium phosphate (anhydrous or dihydrate), sucrose, etc. and mixtures thereof.

In an embodiment, the anti-tacking agent(s) include(s), but not limited to, stearates; stearic acid; vegetable oil; waxes; a blend of magnesium stearate and sodium lauryl sulfate; sodium benzoate; sodium acetate and mixtures thereof.

In an embodiment, the surfactant(s) and emulsifier(s) include(s), but not limited to, ionic or non-ionic surfactants and emulsifiers, poloxamers, polyethylene glycols, polyethylene glycol monostearate, polysorbates, sodium lauryl sulfate, polyethoxylated, hydrogenated castor oil and mixtures thereof.

In an embodiment, the plasticizer(s) include(s), but are not limited to, diethyl phthalate, triethyl citrate, acetyl tributyl citrate, dibutyl phthalate, triacetin, propylene glycol, polyethylene glycol, dichloromethane, acetone, ethanol, methanol, isopropyl alcohol, water and mixtures thereof.

In an embodiment, the stabilizer(s) include(s), but not limited to, gums, agar, taste masking agents like acrylic polymers, copolymers of acrylates, celluloses, resins and mixtures thereof.

In an embodiment, the sweetener(s) include(s), but not limited to, mannitol, sorbitol, polyethylene glycol (PEG) 6000 and 8000, Emdex, Nu-tab, Sweetrex, Mola-tab, Honytab, Sugartab, non-sugar sweetening agents such as aspartame, sorbitol, xylitol, isomalt, saccharin, sodium saccharin, calcium saccharin, sucralose, acesulfame-K, steviol, steviosin, mannitol, erythritol, lactitol, and sugar sweetening agents such as sucrose, fructose, dextrose and mixtures thereof.

Although several embodiments of the present disclosure names few of the commonly used excipients, any other excipient known to or appreciated by a skilled person can also be used to realize the advantageous compositions of the present disclosure. Examples of useful excipients which can optionally be added to the composition are described in the Handbook of Pharmaceutical Excipients, 3rd edition, Edited by A. H. Kibbe, Published by: American Pharmaceutical Association, Washington D.C., ISBN: 0-917330-96-X, and in Handbook of Pharmaceutical Excipients (4th edition), Edited by Raymond C Rowe—Publisher: Science and Practice.

Depending on the intended mode of administration, the pharmaceutical composition may be formulated as a solid, semi-solid or liquid dosage form. Non-limiting examples of dosage forms includes tablet, lozenge, capsule, caplet, modified release tablet or lozenge, suspension, solution, emulsion, suppository, granules, pellets, beads, powder, aerosol sprays (oral, nasal, dermal), cream, ointment, lotion, patches, pre-filled syringe, pre-filled pen, gel, tablet in tablet, bilayer tablet, trilayer tablet, inlay tablet, capsule in capsule, tablet(s) in capsule, granules and/or pellets in capsule, pellets and tablet in capsules and the likes.

In an embodiment, there is disclosed a fixed dose pharmaceutical composition comprising Famotidine or salt or hydrates or solvates thereof, Lidocaine or salt or hydrates or solvates thereof, and Melatonin or salt or hydrates or solvates thereof, wherein the composition is formulated into a chewy or hard or caramel based lozenge, pastilles, troches, soft lozenge, center or liquid filled lozenge, power based lozenge, compressed lozenge, syrup based lozenge, granulated lozenge, buccal and sublingual tablets. The lozenge formulation of the present disclosure may increase bioavailability, reducing gastric irritation and increases onset of action. Lozenges dosage forms are easy to administer for geriatric and pediatric patients who can't swallow tablets formulation. This formulation may help to keep the drug in contact to the oral cavity for longer time. The lozenge may be formulated as a modified release formulation (modified release can be controlled release, immediate release, phased release, timed release, sustained release, delayed release or a combination of immediate or quick or fast and sustained or slow or extended release). The lozenge can be formulated as a bi-layer, tri-layer tablet or multi-layer tablet to facilitate the delivery of at least two or more active agents.

Typically, the carrier material for lozenge preparation includes sugar such as sucrose, dextrose, etc. Recently consumers have become concerned about the excessive levels of sugar contained within their diets. This concern has caused a demand for sugar-free products, including sugar-free medications. Pharmaceutical manufacturers have attempted to find alternative carrier bases in order to provide sugar-free lozenges. One such alternative carrier is a polyhydric alcohol such as xylitol. Polyhydric alcohols are considered as a viable alternative because they provide a sweet taste will mask the bitter taste of many medicinal agents. Lozenges made from polyhydric alcohols do suffer from one serious disadvantage. They dissolve very rapidly when placed in the oral cavity. For example, a lozenge made from a xylitol based carrier will dissolve completely within approximately 3 minutes of administration. Other polyhydric alcohols such as sorbitol or mannitol will also dissolve within 3 minutes of administration. Thus the medicinal agents are released so rapidly that a large percentage of the dose is washed into the patients alimentary canal rather than having an opportunity to come in contact with the tissues of the oral cavity which are under treatment. Thus it would be a valuable contribution to the art to produce polyhydric alcohol based lozenges having slower rates of dissolution within the oral cavity.

In an embodiment, non-limiting examples of excipients for preparing a compressed powder lozenge or compressed granulated lozenge, cast lozenge includes at least one diluents, at least one fillers, at least one glidants, at least one lubricants, at least one binders, at least one preservatives, at least one artificial or natural sweeteners or and at least one aroma or flavoring compounds.

The lozenge may be formulated as a modified release formulation (modified can be controlled release, immediate release, phased release, timed release, sustained release, delayed release or a combination of immediate or quick or fast and sustained or slow or release). The lozenge can be formulated as a bi-layer, tri-layer tablet or multi-layer tablet to facilitate the delivery of at least two or more active agents.

In some embodiments, the compositions are formulated as cast lozenges comprising at least one base selected from fructo-oligosaccharides, crystalline sugar, candy base, isomalt or stevia; at least one aromas selected from natural aroma, essential oils such as citrus, mint oils, terpenes and sesquiterpenes, organic acids, alcohols, aldehydes, liquorice powder, menthol, peppermint oil or any fruit flavors; at least one taste enhancing ingredient such as saccharose, glutamic acid, E621 monosodium glutamate, MSG, E622 monopotassium glutamate, E623 calcium diglutamate, E625 Magnesium diglutamate); guanylic acid (a ribonucleotide) and its salts (E626 guanylic acid, E627 disodium guanylate, sodium guanylate, E628 dipotassium guanylate, E629 calcium guanylate); E630 inosinic acid, E631 disodium inosinate, E632 dipotassium inosinate, E633 calcium inosinate), E634 calcium 5'-ribonucleotides, E635 disodium 5'-ribonucleotides; E636 maltol, E637 ethyl maltol, E640 glycine and E641 L-leucine.

The advantages of drugs administration by the buccal route is the drug is not damaged by acidic media of the stomach, and the achievement of therapeutic serum concentrations of the drug more rapidly. The sublingual route gives greater permeability and has rich blood supply leading to more rapid absorption than other routes.

In an embodiment, there is disclosed a fixed dose pharmaceutical composition comprising Famotidine or salt or hydrates or solvates thereof, Lidocaine or salt or hydrates or solvates thereof, and Melatonin or salt or hydrates or solvates thereof, wherein the composition is formulated into a tablet dosage form. The tablet may be a monolayer tablet comprising Famotidine or salt or hydrates or solvates thereof, Lidocaine or salt or hydrates or solvates thereof and Melatonin or salt or hydrates or solvates thereof in a single uniform layer. The tablet may be a bilayer tablet comprising Famotidine or salt or hydrates or solvates thereof, Lidocaine or salt or hydrates or solvates thereof and Melatonin or salt or hydrates or solvates thereof in any of a first layer and a second layer. Alternatively, the tablet may be a trilayer tablet comprising Famotidine or salt or hydrates or solvates thereof, Lidocaine or salt or hydrates or solvates thereof and Melatonin or salt or hydrates or solvates thereof in any of a first layer, a second layer and a third layer. Alternatively, the tablet may be a press-coated tablet, i.e. a small tablet and a granulation or a blend is compressed together to one large press-coated tablet. All types of the herein before mentioned tablets may be without a coating or may have one or more coatings, in particular film-coatings.

The tablet-in-tablet dosage form may be prepared by compressing active ingredients with one or more rate controlling polymer or non-polymer to form a core extended release tablet; and compressing active ingredients optionally along with one or more pharmaceutically acceptable excipient onto said core tablet to form compressed tablet that causes immediate release of the active ingredients.

In another embodiment of the present invention, the pharmaceutical composition is formulated as an inlay tablet. Inlay tablets are tablets, wherein inner tablet is positioned within a comparatively larger outer tablet in such a way that at least one surface of the inner tablet is not in contact with outer tablet. Inlay tablet dosage form includes: (a) an inner inlayed tablet comprising active ingredients and excipient(s) that causes extended release; and (b) an outer tablet comprising active ingredients along with excipient(s) to cause immediate release.

In another embodiment, the present disclosure embraces capsule-in-capsule formulations, wherein smaller size capsule is encapsulated into a larger capsule. Capsule-in-capsule consists of an external capsule and internal capsule (inner capsule) located therein. It is preferred that smaller size capsule is filled with active ingredients and excipients so as to cause extended release while larger capsule is filled, optionally, with active ingredients along with excipients for immediate release.

The tablet of the present disclosure may be monolithic that means having a homogenous matrix of active ingredient and pharmaceutically acceptable excipients. Alternatively, the tablet may be formed as a bilayer, wherein the one layer is having active ingredients along with pharmaceutically acceptable excipients and other layer is having pharmaceutically acceptable excipients. Alternatively, both layer of bilayer tablet may contain active ingredients.

The composition can be made by different manufacturing processes such as by direct compression, wet granulation, dry granulation, melt granulation, melt congealing, extrusion and the likes. The composition cores may be mono or multi-layer(s) and can be coated with appropriate overcoats as known in the art. Wet granulation involves formation of granules using active ingredient and one or more pharmaceutically acceptable excipients and this portion can be termed as intra-granular portion. These granules are then lubricated with blend of excipients comprising lubricant and this lubricant blend is then compressed to form a tablet. The portion outside the granules can be referred as extra-granular portion. Direct compression on the other hand requires only that the active ingredient is blended with one or more pharmaceutically acceptable excipients before compression and then compressed into tablet. The preferred way for making the composition of the present disclosure is wet granulation.

In an embodiment, there is disclosed a fixed dose pharmaceutical composition comprising Famotidine or salt or hydrates or solvates thereof, Lidocaine or salt or hydrates or solvates thereof, and Melatonin or salt or hydrates or solvates thereof, wherein the composition comprises an intra-granular portion and an extra-granular portion, wherein the intra-granular portion comprises Famotidine or salt or hydrates or solvates thereof, Lidocaine or salt or hydrates or solvates thereof, Melatonin or salt or hydrates or solvates thereof and a pharmaceutically acceptable excipient, and the extra-granular portion comprises a pharmaceutically acceptable excipient.

In another embodiment, there is disclosed a fixed dose pharmaceutical composition comprising Famotidine or salt or hydrates or solvates thereof, Lidocaine or salt or hydrates or solvates thereof, and Melatonin or salt or hydrates or solvates thereof, wherein the composition comprises an intra-granular portion and an extra-granular portion, and wherein the intra-granular portion comprises Lidocaine or salt or hydrates or solvates thereof, Melatonin or salt or hydrates or solvates thereof and a pharmaceutically acceptable excipient, and the extra-granular portion comprises Famotidine or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof, and Melatonin or salt or hydrates or solvates thereof, wherein the composition comprises an intra-granular portion and an extra-granular portion, and wherein the intra-granular portion comprises Famotidine or salt or hydrates or solvates thereof, Melatonin or salt or hydrates or solvates thereof and a pharmaceutically acceptable excipient, and the extra-granular portion comprises Lidocaine or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, and wherein the intra-granular portion comprises Famotidine or salt or hydrates or solvates thereof and Lidocaine or salt or hydrates or solvates thereof and a pharmaceutically acceptable excipient, and the extra-granular portion comprises Melatonin or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, and wherein the intra-granular portion comprises Famotidine or salt or hydrates or solvates thereof and a pharmaceutically acceptable excipient, and the extra-granular portion comprises Melatonin or salt or hydrates or solvates thereof, Lidocaine or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, and wherein the intra-granular portion comprises Lidocaine or salt or hydrates or solvates thereof and a pharmaceutically acceptable excipient, and the extra-granular portion comprises Famotidine or salt or hydrates or solvates thereof, Melatonin or salt or hydrates or solvates thereof and a pharmaceutically acceptable excipient.

In yet another embodiment, there is disclosed a fixed dose pharmaceutical composition comprising Famotidine or salt or hydrates or solvates thereof, Lidocaine or salt or hydrates or solvates thereof and Melatonin or salt or hydrates or solvates thereof, wherein the composition comprises an intra-granular portion and an extra-granular portion, and wherein the intra-granular portion comprises Melatonin or salt or hydrates or solvates thereof and a pharmaceutically acceptable excipient and the extra-granular portion comprises Famotidine or salt or hydrates or solvates thereof and Lidocaine or salt or hydrates or solvates thereof and a pharmaceutically acceptable excipient.

In one embodiment, the portions are compressed together to obtain any of a tablet dosage form or a lozenge dosage form, optionally coated with a seal coat. In an embodiment, the seal coat is an aqueous seal coat.

All types of the tablets mentioned hereinabove may be without a coating or may have one or more coatings, in particular film-coatings. A film coating may aid in limiting photolytic degradation and/or in limiting degradation of moisture sensitive materials.

In on embodiment, the tablet may be coated to delay disintegration and/or absorption and thereby provide sustained action over a longer period. The non-limiting examples of film coating includes glyceryl monostearate or glyceryl distearate, polyvinyl alcohol based coatings, hydroxyethylcellulose, hydroxypropylmethylcellulose, sodium carboxymethylcellulose, polyethelene glycol 4000 and cellulose acetate phthalate film coating.

The compositions realized in accordance with embodiments of the present disclosure can find utility in treatment of mucositis, oral mucositis, gastritis, peptic ulcers, gastric ulcer, duodenal ulcer, esophageal ulcer, stomatitis, gastroesophageal reflux disease (GERD), esophagitis, Zollinger Ellison syndrome, radiation induced esophagitis, and the like oral and gastrointestinal conditions. Without wishing to be bound by the theory, it is believed that the combination of Famotidine or salt or hydrates or solvates thereof, Lidocaine or salt or hydrates or solvates thereof, and Melatonin or salt or hydrates or solvates thereof, in particular, the fixed dose compositions disclosed herein, afford treatment of oral mucositis, radiation induced esophagitis, stomatitis and ulcers from root cause by targeting inflammatory mediators, by relieving pain, by increasing the expression and activity of endogenous antioxidant enzymes and by targeting histamine receptors, which are normally upregulated in oral cancers triggering ulceration (H2) providing effective pain relief. The compositions of the present disclosure also reduce the amount of acid released in the digestive tract, which relieves gastritis pain and healing of ulcers as well as can act in the gastric region to relieve abdominal, gastric pain, and heartburn associated with ulcer, indigestion, and bleeding. The compositions of the present disclosure can also afford anti-inflammatory and mucosal repair mechanism to strengthen the gastric mucosal barrier by reducing oxidative stress caused by various irritants (such as NSAIDs) including bacterial infection by *H. pylori*. Preliminary study on assessment of the ulceration index (UI) in rodents revealed marked improvement in irritant induced ulcers establishing the efficacy of the presently disclosed compositions. It could also be noted that the components of the compositions realized in accordance with embodiments of the present disclosure exhibit high degree of functional reciprocity by targeting different pathways and consequently, afford unique treatment options for mucositis, stomatitis, radiation induced esophagitis, oral mucositis, gastritis and related pain, which may be due to elevated levels of gastric acid secretion and/or ulceration induced by *H. pylori*, NSAIDs and the likes. Without wishing to be bound by the theory, it is also believed that the compositions realized in accordance with embodiments of the present disclosure exhibit high degree of functional reciprocity, wherein one or more active agents of the composition aids in retarding metabolism of the other active agent(s), and consequently, may reduce the dosage requirements and/or may aid in affording a prolonged action/efficacy. Specifically, it is believed that Famotidine undergoes metabolism (about 25-30%) through Cytochrome P450 system (CYP1A2) and excretion thereof may be decreased when combined with Melatonin. Similarly, Lidocaine undergoes metabolism through Cytochrome P450 system (CYP3A4) and metabolism thereof may be decreased when combined with Famotidine. Similarly, Melatonin undergoes metabolism through Cytochrome P450 system (CYP1A1) and metabolism thereof can be decreased when combined with lidocaine.

Accordingly, an embodiment of the present disclosure provides a method of treatment of oral mucositis in a subject, said method comprising administering to a subject in need thereof an effective amount of a pharmaceutical composition comprising Famotidine or salt or hydrates or solvates thereof, Lidocaine or salt or hydrates or solvates thereof, and Melatonin or salt or hydrates or solvates thereof.

Another embodiment of the present disclosure provides a method of treatment of a gastrointestinal condition, said method comprising administering to a subject in need thereof an effective amount of a pharmaceutical composition comprising Famotidine or salt or hydrates or solvates thereof, Lidocaine or salt or hydrates or solvates thereof, and Melatonin or salt or hydrates or solvates thereof. The gastrointestinal conditions may be gastritis, mucositis, gastroesophageal reflux or heartburn, radiation induced esophagitis, ulcer, esophagitis, Zollinger Ellison syndrome and the like conditions, which are associated with elevated levels of gastric acid and/or an infection by *H. pylori* and/or administration of gastric irritants (such as NSAIDs, chemotherapy, radiotherapy and the likes).

Further embodiment of the present disclosure provides a pharmaceutical composition for use in treatment of oral mucositis, said composition comprising Famotidine or salt or hydrates or solvates thereof, Lidocaine or salt or hydrates or solvates thereof, and Melatonin or salt or hydrates or solvates thereof.

Still further embodiment of the present disclosure provides a pharmaceutical composition for use in treatment of a gastrointestinal condition, said composition comprising Famotidine or salt or hydrates or solvates thereof, Lidocaine or salt or hydrates or solvates thereof, and Melatonin or salt or hydrates or solvates thereof. The gastrointestinal conditions may be gastritis, mucositis, radiation induced esophagitis, gastroesophageal reflux or heartburn, esophagitis, Zollinger Ellison syndrome, ulcer and the like conditions, which are associated with elevated levels of gastric acid and/or an infection by *H. pylori* and/or administration of gastric irritants (such as NSAIDs, chemotherapy, radiotherapy and the likes).

Yet another embodiment of the present disclosure provides use of a pharmaceutical composition for manufacture of a medicament for treatment of oral mucositis, said composition comprising Famotidine or salt or hydrates or solvates thereof, Lidocaine or salt or hydrates or solvates thereof, and Melatonin or salt or hydrates or solvates thereof.

Yet another embodiment of the present disclosure provides use of a pharmaceutical composition for manufacture of a medicament for treatment of a gastrointestinal condition, said composition comprising Famotidine or salt or hydrates or solvates thereof, Lidocaine or salt or hydrates or solvates thereof, and Melatonin or salt or hydrates or solvates thereof. The gastrointestinal conditions may be gastritis, mucositis, gastroesophageal reflux or heartburn, esophagitis, Barrett's esophagus, radiation induced esophagitis, Esophageal cancer, gastric cancer complications, Zollinger Ellison syndrome, ulcer, symptomatic relief of symptoms in cancer (palliative care) and the like conditions, which are associated with elevated levels of gastric acid and/or an infection by *H. pylori* and/or administration of gastric irritants (such as NSAIDs, chemotherapy, radiotherapy and the likes).

Further embodiment of the present disclosure provides a pharmaceutical composition for treatment of oral mucositis, said composition comprising Famotidine or salt or hydrates or solvates thereof, Lidocaine or salt or hydrates or solvates thereof, and Melatonin or salt or hydrates or solvates thereof.

Further embodiment of the present disclosure provides a pharmaceutical composition for treatment of a gastrointestinal condition, said composition comprising Famotidine or salt or hydrates or solvates thereof, Lidocaine or salt or hydrates or solvates thereof, and Melatonin or salt or hydrates or solvates thereof. The gastrointestinal conditions may be gastritis, mucositis, gastroesophageal reflux or heartburn, ulcer, esophagitis, Zollinger Ellison syndrome, radiation induced esophagitis, and the like conditions, which are associated with elevated levels of gastric acid and/or an infection by *H. pylori* and/or administration of gastric irritants (such as NSAIDs, chemotherapy, radiotherapy and the likes).

The compositions of the present disclosure affords increased therapeutic effects, and reduced adverse effects, making these pharmaceutical compositions extremely effective therapeutics, especially in the treatment of oral, gastrointestinal and esophageal disorders or diseases. Therapeutic levels of the combined drugs will vary from individual to individual and progression stage of disease. The combination medications in the appropriate amounts and intervals effective to treat oral, gastrointestinal and esophageal disorders or diseases will necessarily be monitored both clinically and chemically by the medical experts or trained physicians. The relevant formulation can eventually take the form of a combined pill given daily, a daily or weekly patch, a long-term injection, an implant, or a short-acting or long-acting form of medication.

Further, the patient may receive the specific dosage over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like.

The choice of appropriate dosages for the drugs used in combination therapy according to the present disclosure can be determined and optimized by the skilled artisan, e.g., by observation of the patient, including the patient's overall health, the response to the combination therapy, and the like. Optimization, for example, may be necessary if it is determined that a patient is not exhibiting the desired therapeutic effect or conversely, if the patient is experiencing undesirable or adverse side effects that are too many in number or are of a troublesome severity.

It is especially advantageous to formulate compositions of the present disclosure in unit dosage form for ease of administration and uniformity of dosage. The specifications of the dosage unit forms of the present disclosure are dependent on the unique characteristics of the composition and the particular therapeutic effect to be achieved. Dosages can further be determined by reference to the usual dose and manner of administration of the ingredients. Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995).

EXAMPLES

Fatty Acid Derivatives

Scheme I: Synthesis of 4-((1,3-bis(octanoyloxy)propan-2-yl)oxy)-4-oxobutanoic acid (diglyceryl capryl succinate)

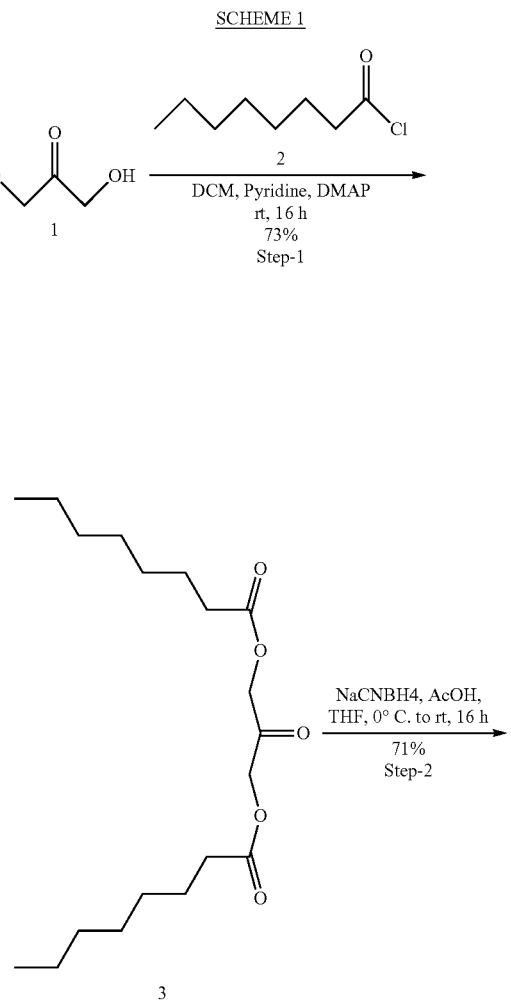

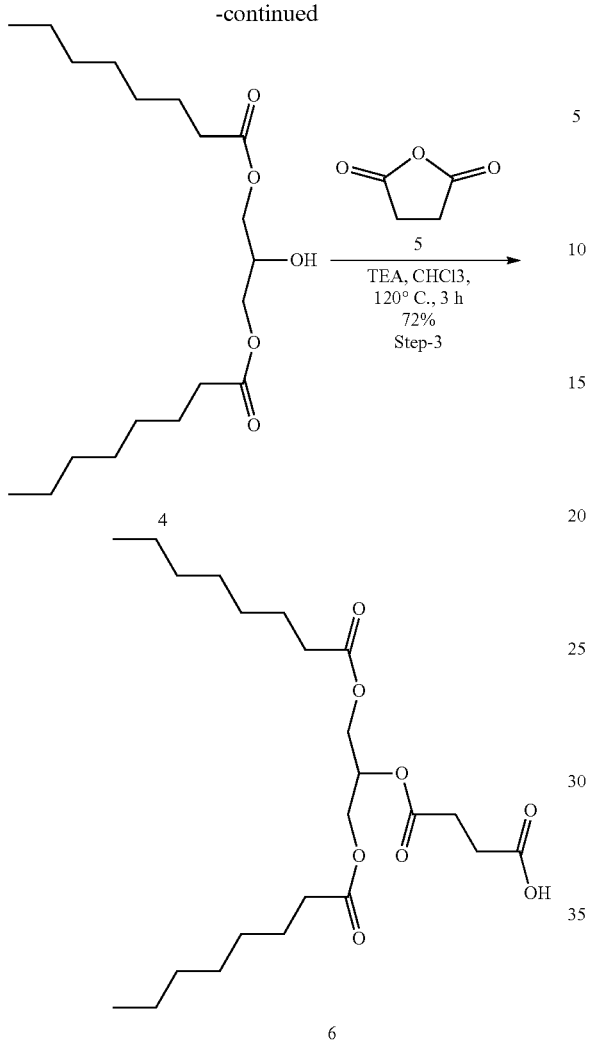

Step 1: Synthesis of 2-oxopropane-1,3-diyl dioctanoate (3): To an ice cold solution of 1,3-dihydroxypropan-2-one (1, 25.0 g, 0.277 mol) in dichloromethane (500 mL) was added 4-dimethylaminopyridine (10.17 g, 0.083 mol) and pyridine (49.2 mL, 0.610 mol) and stirred for next 5 min. To the above mixture octanoyl chloride (2, 105.4 mL, 0.610 mol) was added dropwise at 0° C., and the reaction mixture was stirred at room temperature for 16 h. After completion, reaction mixture was filtered; the solid was washed with dichloromethane (100 mL), filtrate was washed with brine (200 mL), saturated solution of sodium bicarbonate (200 mL) and 0.1 N HCl solution (100 mL). Organic layer was separated and dried over anhydrous sodium sulfate and solvent was removed under reduced pressure to get crude. The crude was purified by silica gel (100-200 mesh) column chromatography eluting with 10% ethyl acetate in hexanes to afford the desired product as white solid. Yield: 70.0 g, 73%. MS (ESI) m/z 343.19 [M+1]$^+$; $^1$H NMR (400 MHz, DMSO-d6); δ 4.84 (s, 4H), 2.37 (t, J=7.2 Hz, 4H), 1.45-1.62 (m, 4H), 1.15-1.35 (m, 16H), 0.78-0.92 (m, 6H).

Step 2: Synthesis of 2-hydroxypropane-1,3-diyl dioctanoate (4): To an ice cold solution of 2-oxopropane-1,3-diyl dioctanoate (3, 70.0 g, 0.204 mol) in THF (1000 mL) was added drop wise acetic acid (15 mL), followed by the portion wise addition of sodium cyanoborohydride (15.43 g, 0.245 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude thus obtained was purified by silica gel (100-200 mesh) column chromatography eluting with 12 to 15% ethyl acetate in hexanes to afford the desired product 4 as yellow liquid. Yield: 50.0 g, 71%. MS (ESI)– m/z 345.29 [M+1]$^+$; $^1$H NMR (400 MHz, DMSO-d6); δ 5.25 (d, =5.2 Hz, 1H), 3.92-4.03 (m, 4H), 3.81-3.90 (m, 1H), 2.29 (t, J=7.6 Hz, 4H), 1.45-1.59 (m, 4H), 1.12-1.35 (m, 16H), 0.85 (t, J=6.8 Hz, 6H).

Step 3: Synthesis of 4-((1,3-bis(octanoyloxy)propan-2-yl)oxy)-4-oxobutanoic acid (6): To a solution of 2-hydroxypropane-1,3-diyl dioctanoate (4, 50.0 g, 0.145 mol) in chloroform (200 mL), dihydrofuran-2,5-dione (5, 17.44 g, 0.174 mol) and triethylamine (30.0 mL, 0.218 mol) were added at room temperature. The reaction mixture was stirred at 120° C. for 3 h. After completion, reaction mixture was diluted with water (200 mL) and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 10 to 15% ethyl acetate in hexanes to afford the desired product 6 as white solid. Yield: 47.0 g, 72%. MS (ESI)– m/z 443.2 [M–1]; $^1$H NMR (400 MHz, DMSO-d6): δ 12.22 (s, 1H), 5.12-5.22 (m, 1H), 4.18-4.25 (m, 2H), 4.09-4.17 (m, 2H), 2.42-2.50 (m, 4H), 2.29 (t, J=7.24 Hz, 4H), 1.44-1.55 (m, 4H), 1.15-1.31 (m, 16H), 0.79-0.90 (m, 6H).

Scheme II: Synthesis of 4-((1,3-bis(dodecanoyloxy)propan-2-yl)oxy)-4-oxobutanoic acid (diglyceryl lauryl succinate)

SCHEME II

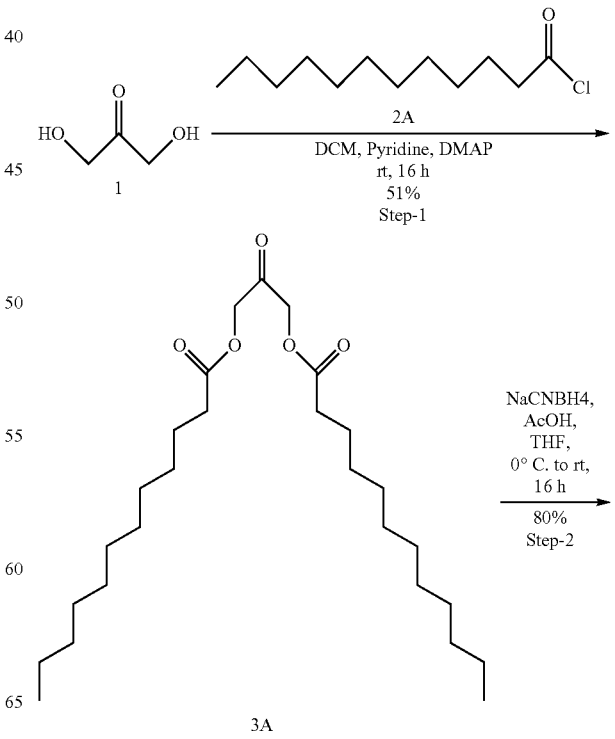

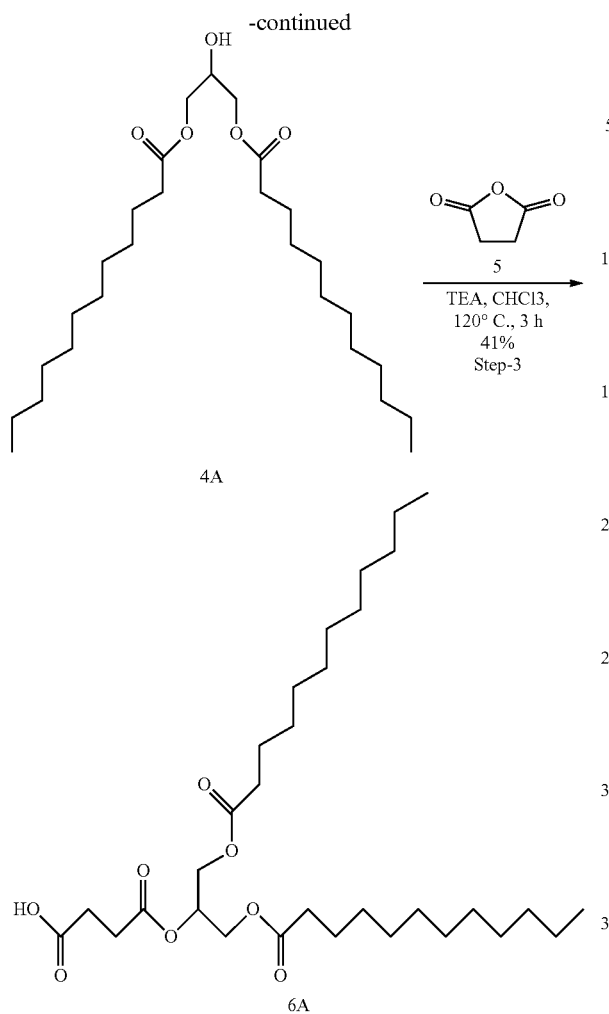

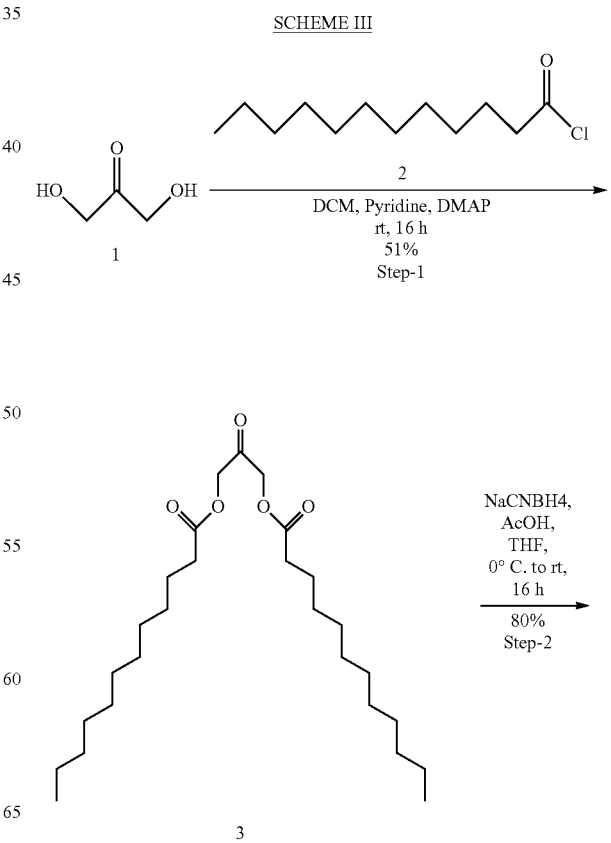

Step 1: Synthesis of 2-oxopropane-1,3-diyl didodecanoate (3A): To an ice cold solution of 1,3-dihydroxypropan-2-one (1, 30.0 g, 0.33 mol) in dichloromethane (500 mL) was added 4-dimethylaminopyridine (20.30 g, 0.167 mol) and pyridine (107 mL, 0.1.332 mol) and stirred for next 5 min. To the above mixture dodecanoyl chloride 2A (218.50 g, 1.167 mol) was added dropwise at 0° C. and the reaction mixture was stirred at room temperature for 16 h. After completion, reaction mixture was filtered; the solid was washed with dichloromethane (100 mL), filtrate was washed with brine (200 mL), saturated solution of sodium bicarbonate (200 mL) and 0.1 N HCl solution (100 mL). Organic layer was separated and dried over anhydrous sodium sulfate and solvent was removed under reduced pressure to get crude. The crude was triturated with diethyl ether to afford the desired product 3A as white solid. Yield: 78 g, 51%. MS (ESI) m/z 455.37 [M+1]$^+$; $^1$H NMR (400 MHz, DMSO-d6)—δ 4.74 (s, 4H), 2.43 (m, 4H), 1.64 (m, 4H), 1.55-1.25 (m, 32H), 0.87 (m, 6H).

Step 2: Synthesis of 2-hydroxypropane-1,3-diyl didodecanoate (4A): To an ice cold solution of 2-oxopropane-1,3-diyl didodecanoate 3A (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4A as white solid. Yield: 60.0 g, 80%. MS (ESI); m/z 457.48 [M+1]; $^1$H NMR (400 MHz, DMSO-d6)—δ 5.26 (d, J=5.2 Hz, 111), 3.92-3.98 (m, 411), 2.28 (m, 411), 1.50 (m, 4H), 1.23 (m, 3311), 0.83 (m, 6H).

Step 3: Synthesis of 4-((1,3-bis(dodecanoyloxy)propan-2-yl)oxy)-4-oxobutanoic acid (6A): To a solution of 2-hydroxypropane-1,3-diyl didodecanoate 4A (40.0 g, 0.087 mol) in chloroform (200 mL), dihydrofuran-2,5-dione 5 (10.50 g, 0.105 mol) and triethylamine (18.50 mL, 0.131 mol) were added at room temperature. The reaction mixture was stirred at 120° C. for 3 h. After completion, reaction mixture was diluted with water (200 mL) and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 25 to 30% ethyl acetate in hexanes to afford the desired product 6A as white solid. Yield: 20.0 g, 41%. MS (ESI) m/z 555.40 [M−1]; $^1$H NMR (400 MHz, DMSO-d6) δ 12.30 (s, 1H), 5.17 (m, 1H), 4.18-4.25 (m, 4H), 2.50-2.47 (m, 8H), 1.23-1.25 (m, 36H), 0.83 (m, 6H).

Scheme III: Synthesis of (E)-4-((1,3-bis(dodecanoyloxy)propan-2-yl)oxy)-4-oxobut-2-enoic acid (diglyceryl lauryl fumarate)

SCHEME III

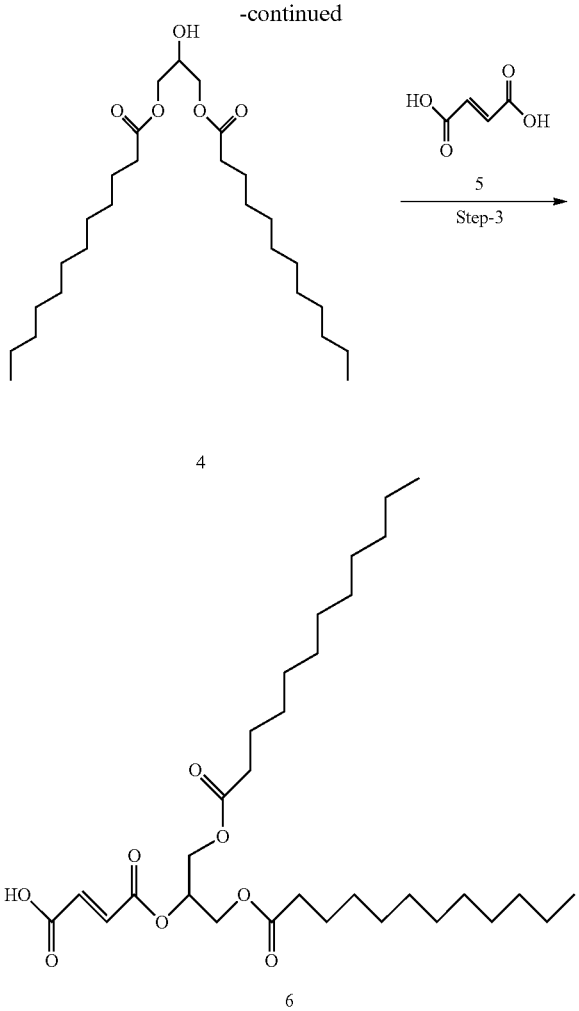

Step 1—Synthesis of 2-oxopropane-1,3-diyl didodecanoate (3*): To an ice cold solution of 1,3-dihydroxypropan-2-one (1, 30.0 g, 0.33 mol) in dichloromethane (500 mL) was added 4-dimethylaminopyridine (20.30 g, 0.167 mol) and pyridine (107 mL, 0.1.332 mol) and stirred for next 5 min. To the above reaction mixture dodecanoyl chloride 2 (218.50 g, 1.167 mol) was added dropwise at 0° C. and the reaction mixture was stirred at room temperature for 16 h. After completion, reaction mixture was filtered, the solid was washed with dichloromethane (100 mL), filtrate was washed with brine (200 mL), saturated solution of sodium bicarbonate (200 mL) and 0.1 N HCl solution (100 mL). The organic layer was separated, dried over anhydrous sodium sulfate and solvent was removed under reduced pressure to get crude. The crude was triturated with diethyl ether to afford the desired product 3* as white solid. Yield: 78 g, 51%. MS (ESI) m/z 455.37 [M+1]$^+$; 1H NMR (400 MHz, DMSO-d6): δ 4.74 (s, 4H), 2.43 (m, 4H), 1.64 (m, 4H), 1.55-1.25 (m, 32H), 0.87 (m, 61H).

Step-2: Synthesis of 2-hydroxypropane-1,3-diyl didodecanoate (4*): To an ice cold solution of 2-oxopropane-1,3-diyl didodecanoate 3 (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4* as white solid. Yield: 60.0 g, 80%. MS (ESI) m/z 457.48 [M+1]$^+$; 1H NMR (400 MHz, DMSO-d6): δ 5.26 (d, J=5.2 Hz, 1H), 3.92-3.98 (m, 4H), 2.28 (m, 4H), 1.50 (m, 4H), 1.23 (m, 33H) and 0.83 (m, 6H).

Step-3: Synthesis of (E)-4-((1,3-bis(dodecanoyloxy)propan-2-yl)oxy)-4-oxobut-2-enoic acid (6*): To an ice-cold solution of 2-hydroxypropane-1,3-diyl didodecanoate 4 (10.0 g, 21.91 mmol) in THF (170 mL) was added fumaric acid 5 (2.54 g, 21.91 mmol), benzoyl chloride (2.5 mL, 21.91 mmol) and DMAP (0.67 g, 5.477 mmol). The resulting mixture was stirred at RT for 16 h. After completion of reaction (TLC monitoring), reaction mixture was concentrated under reduced pressure. The crude was diluted with water (200 mL), adjust pH~2-3 using 1N-HCl and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 80% ethyl acetate in hexanes to afford the desired product 6* as white solid. Yield: 400 mg, 3.30% (un-optimized yield). LC-MS: m/z 553.64 [M−1]; 97.27% purity. 1H NMR (400 MHz, DMSO-d6): δ 13.26 (br s, 1H), 5.17 (d, J=15.8 Hz, 21), 5.29 (m, III), 4.30-4.33 (m, 211), 4.19-4.23 (m, 211), 2.28 (m, 411), 1.48 (m, 4H), 1.22 (m, 32H) and 0.83 (m, 6H).

Non-Limiting Exemplary Compositions
Batch ACGCP300220003B

TABLE 1

Composition for Famotidine, Lidocaine and Melatonin Lozenges

| S. No. | Ingredients | Amount mg/tab | % w/w |
|---|---|---|---|
| I | Intra-granular | | |
| 1 | Famotidine | 40.00 | 6.15 |
| 2 | Lidocaine hydrochloride monohydrate | 100.00 | 15.38 |
| 3 | Melatonin | 10.00 | 1.54 |
| 4 | Mannitol | 354.35 | 54.52 |
| 5 | L-Carnosine | 7.00 | 1.08 |
| 6 | Diglyceryl lauryl fumarate (DGLF) | 10.00 | 1.54 |
| 7 | Heavy magnesium oxide | 25.00 | 3.85 |
| 8 | Calcium carbonate | 25.00 | 3.85 |
| 9 | Croscarmellose sodium | 13.00 | 2.00 |
| II | Binder solution | | |
| 10 | Hypromellose 5 cps | 16.00 | 2.46 |
| 11 | Simethicone 30% emulsion | 25.00 | 3.85 |
| 12 | Water | q.s | q.s |
| III | Extra-granular | | |
| 13 | Croscarmellose sodium | 10.00 | 1.54 |
| 14 | Colloidal Silicon Dioxide | 6.65 | 1.02 |
| 15 | Zinc stearate | 6.50 | 1.00 |
| 16 | Peppermint flavor | 6.50 | 1.00 |
| | Total | 655.00 | 100% |

Method of preparation of Famotidine, Lidocaine and Melatonin Lozenge

I. Granulation
  i. Step 1—Dispensing: Dispensed all the required raw materials using a calibrated weighing balance.
  ii. Step 2—Sifting: Famotidine, Lidocainehydrochloride monohydrate, Melatonin, Mannitol, L-Carnosine, Diglyceryl lauryl fumarate, Magnesium oxide, Calcium carbonate, Croscarmellose sodium were sifted through ASTM #40 sieve.

iii. Step 3—Dry mixing: The sifted mixture was dry mixed in Rapid Mixer Granulator for 10 min.
iv. Step 4—Binder solution preparation: Hypromellose 5 cps was dissolved in water and mixed well followed by the addition of Simethicone.
v. Step 5—Wet Mixing: The dry mix obtained in step 3 was granulated using binder solution prepared in step 4 to obtain granules.
vi. Step 6—Drying: Granules obtained in step 5 were dried at an inlet temperature of NMT 60° C. until LOD of NMT 4.5% is obtained.
vii. Step 7—Sizing: Dried granules were passed through ASTM sieve no. 40.
viii. Step 8—Pre-Lubrication: Granules of step 7 were blended with extra-granular materials (passed through ASTM 40 sieve) i.e., Croscarmellose sodium, colloidal silicon dioxide and peppermint flavor and blended for 10 min.
ix. Step 9—Lubrication: Blend obtained in step 8 was lubricated with #60 passed zinc stearate for 5 min.

II. Compression:
Lubricated blend obtained in step 9 was compressed. Compression parameters are provided in Table 2 below:

TABLE 2

Compression parameters

| Parameter | Observations |
|---|---|
| Average weight (mg) | 655 |
| Hardness (kP) | 5-6 |
| Thickness (mm) | 5.05-5.15 |
| Disintegration time (min) | 8-9 |
| Observation | No sticking observed, flow of blend was good |

III. Packaging:
The obtained tablets were packed in 60 cc HDPE bottle along with one 2 g silica gel bag, induction sealed and closed with 33 mm CR closure.

IV. Stability and Release Profile:
Stability and release parameters of the lozenges were tested, results whereof are provided in Table 3 below.

TABLE 3

Stability and drug release profile of lozenges
Container Closure 60 cc HDPE bottle/33 mm CR closure with two 1 g silica gel bags

| Test Parameters | Initial | 40° C./75% RH - 1M | 40° C./75% RH - 2M | 40° C./75% RH - 3M | 25° C./60% RH - 3M |
|---|---|---|---|---|---|
| Description | Complies | Complies | Complies | Complies | Complies |
| Assay (%) | | | | | |
| Famotidine | 101.0 | 100.4 | 101.5 | 100.3 | 99.0 |
| Lidocaine hydrochloride | 103.0 | 97.9 | 98.1 | 102.6 | 99.4 |
| Melatonin | 102.9 | 102.0 | 102.9 | 102.4 | 101.1 |
| Water content | 3.20 | 3.50 | 3.10 | 2.98 | 2.91 |
| Related Substances (%) | | | | | |
| Famotidine IMP-A | ND | ND | ND | ND | ND |
| Famotidine IMP-B | 0.021 | 0.022 | 0.018 | 0.018 | 0.015 |
| Famotidine IMP-C | 0.006 | 0.008 | 0.048 | 0.064 | 0.012 |
| Famotidine IMP-D | 0.018 | 0.035 | 0.050 | 0.073 | 0.011 |
| Famotidine IMP-E | ND | 0.040 | 0.031 | 0.042 | 0.013 |
| Famotidine IMP-F | 0.010 | 0.028 | 0.017 | 0.024 | 0.011 |
| Famotidine IMP-G | 0.022 | 0.051 | 0.048 | 0.040 | 0.042 |
| Famotidine IMP-H | 0.021 | 0.027 | 0.023 | 0.022 | 0.019 |
| Famotidine IMP-I | 0.052 | 0.038 | 0.021 | 0.025 | 0.057 |
| Famotidine IMP-J | ND | ND | ND | ND | ND |
| Lidocaine IMP-H | ND | ND | ND | ND | ND |
| Melatonin IMP-A | 0.034 | 0.031 | ND | ND | ND |
| Any unknown highest of Famotidine @ 1.284 | 0.014 | 0.055 | 0.081 | 0.093 | 0.024 |
| Any unknown highest of Lidocaine @ 0.559 | 0.008 | 0.042 | 0.033 | 0.044 | 0.014 |
| Any unknown highest of Melatonin @ 0.812 | 0.069 | 0.058 | 0.080 | 0.068 | 0.073 |
| Total Impurities | 0.349 | 0.680 | 0.634 | 0.683 | 0.436 |

Dissolution Methodology: Medium: pH 6.8 Phosphate buffer, Speed: 50 RPM, Volume: 900 mL, Appts: USP II

| Time (min) | % drug release | % drug release | % drug release |
|---|---|---|---|
| Famotidine | | | |
| 5 min | 17 | 6 | 10 |
| 10 min | 36 | 12 | 22 |
| 15 min | 56 | 21 | 34 |
| 30 min | 69 | 51 | 63 |
| 45 min | 76 | 65 | 71 |
| 60 min | 79 | 71 | 77 |
| 90 min | 83 | 77 | 83 |
| 120 min | 86 | 81 | 86 |

TABLE 3-continued

Stability and drug release profile of lozenges
Container Closure 60 cc HDPE bottle/33 mm CR closure with two 1 g silica gel bags

| Lidocaine Hydrochloride | | | |
|---|---|---|---|
| 5 min | 24 | 8 | 17 |
| 10 min | 49 | 19 | 37 |
| 15 min | 77 | 30 | 56 |
| 30 min | 94 | 77 | 92 |
| 45 min | 99 | 91 | 97 |
| 60 min | 102 | 95 | 100 |
| 90 min | 104 | 97 | 103 |
| 120 min | 105 | 98 | 104 |
| Melatonin | | | |
| 5 min | 26 | 9 | 18 |
| 10 min | 53 | 20 | 37 |
| 15 min | 79 | 32 | 54 |
| 30 min | 95 | 80 | 87 |
| 45 min | 99 | 93 | 91 |
| 60 min | 102 | 98 | 94 |
| 90 min | 103 | 100 | 97 |
| 120 min | 104 | 101 | 98 |

Batch ACGCP300220001B

Lozenges were prepared using the composition as provided in Table 4 below:

TABLE 4

Composition for Famotidine, Lidocaine and Melatonin Lozenges

| Ingredients | mg/Unit | % w/w |
|---|---|---|
| Granulation 1 (Intra-granular) | | |
| Famotidine | 40.00 | 6.15 |
| Lidocaine hydrochloride monohydrate | 100.00 | 15.38 |
| L-Carnosine | 10.00 | 1.54 |
| Xylitol | 307.60 | 47.32 |
| Heavy magnesium oxide | 25.00 | 3.85 |
| Calcium carbonate | 25.00 | 3.85 |
| Simethicone | 25.00 | 3.85 |
| Croscarmellose sodium | 6.50 | 1.00 |
| Granulation 2 (Intra-granular) | | |
| Melatonin | 10.00 | 1.54 |
| DGLF | 10.00 | 1.54 |
| Xylitol | 59.90 | 9.22 |
| Hypromellose 5 cps | 10.00 | 1.54 |
| Extra granular | | |
| Croscarmellose sodium | 6.50 | 1.00 |
| Colloidal Silicon Dioxide | 1.50 | 0.23 |
| Zinc stearate | 6.50 | 1.00 |
| Peppermint flavor | 6.50 | 1.00 |
| Water | qs | q.s |
| Average tablet weight | 650.00 | 100.00 |

Note:
Over granulation of blend was observed during granulation.

Batch ACGCP300220002B

Lozenges were prepared using the composition as provided in Table 5 below:

TABLE 5

Composition for Famotidine, Lidocaine and Melatonin Lozenges

| Ingredients | mg/Unit | % w/w |
|---|---|---|
| Granulation | | |
| Famotidine | 40.00 | 6.15 |
| Lidocaine hydrochloride monohydrate | 100.00 | 15.38 |
| Melatonin | 10.00 | 1.54 |
| Xylitol 90 | 351.35 | 54.05 |
| L-Carnosine | 10.00 | 1.54 |
| DGLF | 10.00 | 1.54 |
| Heavy magnesium oxide | 25.00 | 3.85 |
| Calcium carbonate | 25.00 | 3.85 |
| Croscarmellose sodium | 13.00 | 2.00 |
| Binder solution | | |
| Hypromellose 5 cps | 16.00 | 2.46 |
| Simethicone | 25.00 | 3.85 |
| Water | q.s | q.s |
| Extra granular | | |
| Croscarmellose sodium | 10.00 | 1.54 |
| Colloidal Silicon Dioxide | 1.65 | 0.25 |
| Zinc stearate | 6.50 | 1.00 |
| Peppermint flavor | 6.50 | 1.00 |
| Average tablet weight | 650.00 | 100.00 |

Note:
Over granulation of blend was observed during granulation.

Batch ACGCP300220005B

Lozenges were prepared using the composition as provided in Table 6 below:

TABLE 6

Composition for Famotidine, Lidocaine and Melatonin Lozenges

| Ingredients | mg/Unit | % w/w |
|---|---|---|
| Granulation | | |
| Famotidine | 40.00 | 5.97 |
| Lidocaine hydrochloride monohydrate | 100.00 | 14.93 |
| Melatonin | 10.00 | 1.49 |
| Xylitol | 356.50 | 53.21 |
| DGLF | 10.00 | 1.49 |
| Heavy magnesium oxide | 25.00 | 3.73 |

TABLE 6-continued

Composition for Famotidine, Lidocaine and Melatonin Lozenges

| Ingredients | mg/Unit | % w/w |
|---|---|---|
| Calcium carbonate | 25.00 | 3.73 |
| Croscarmellose sodium | 13.00 | 1.94 |
| Binder solution | | |
| Hypromellose 5 cps | 16.00 | 2.39 |
| Simethicone | 25.00 | 3.73 |
| Isopropyl alcohol | q.s | q.s |
| Extra granular | | |
| Croscarmellose sodium | 25.00 | 3.73 |
| Colloidal Silicon Dioxide | 10.00 | 1.49 |
| Zinc stearate | 8.00 | 1.19 |
| Peppermint flavor | 6.50 | 0.97 |
| Average tablet weight | 670.00 | 100.00 |

TABLE 7

Compression parameters

| Parameter | Observations |
|---|---|
| Toolings | 13.00 mm round |
| Average tablet weight (mg) | 670 mg |
| Tablet hardness (kP) | 3-4 kp |
| Disintegration time (min) | 31-35 min |
| Remarks | Free flowing blend |

TABLE 8

Dissolution in pH 6.8 Phosphate buffer
Initial

| Time | Famotidine Average | Lidocaine Average | Melatonin Average |
|---|---|---|---|
| 5 Min | 3 | 9 | 5 |
| 10 Min | 5 | 12 | 8 |
| 15 Min | 8 | 15 | 11 |
| 30 Min | 13 | 22 | 19 |
| 45 Min | 21 | 31 | 30 |
| 60 Min | 31 | 42 | 42 |
| 90 min | 47 | 60 | 60 |
| 120 min | 71 | 86 | 88 |

Batch ACGCP300220006B

Lozenges were prepared using the composition as provided in Table 9 below:

TABLE 9

Composition for Famotidine, Lidocaine and Melatonin Lozenges

| Ingredients | mg/Unit | % w/w |
|---|---|---|
| Granulation (Intra-granular) | | |
| Famotidine | 40.00 | 6.15 |
| Melatonin | 10.00 | 1.54 |
| Xylitol | 326.75 | 50.27 |
| L-Carnosine | 10.00 | 1.54 |
| Diglyceryl lauryl fumarate(DGLF) | 10.00 | 1.54 |
| Heavy magnesium oxide | 25.00 | 3.85 |
| Calcium carbonate | 25.00 | 3.85 |
| Croscarmellose sodium | 13.00 | 2.00 |

TABLE 9-continued

Composition for Famotidine, Lidocaine and Melatonin Lozenges

| Ingredients | mg/Unit | % w/w |
|---|---|---|
| Binder solution | | |
| Hypromellose 5 cps | 16.00 | 2.46 |
| Simethicone | 25.00 | 3.85 |
| Water | q.s | q.s |
| Extra granular | | |
| Lidocaine hydrochloride monohydrate | 100.00 | 15.38 |
| Xylitol | 20.00 | 3.08 |
| Croscarmellose sodium | 13.00 | 2.00 |
| Colloidal Silicon Dioxide | 3.25 | 0.50 |
| Zinc stearate | 6.50 | 1.00 |
| Peppermint flavor | 6.50 | 1.00 |
| Average tablet weight | 650.00 | 100.00 |

Note:
Over granulation of blend was observed during granulation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

I claim:

1. A pharmaceutical composition formulated as an oral dosage form comprising: Famotidine or a salt thereof in an amount ranging from 10 mg to 100 mg, Lidocaine or a salt thereof in an amount ranging from 50 mg to 400 mg, and Melatonin or a salt thereof in an amount ranging from 1 mg to 60 mg.

2. The composition of claim 1, wherein the oral dosage form is selected from a group consisting of a lozenge, tablet, suspension, solution and emulsion.

3. The composition of claim 1, wherein the oral dosage form is selected from a group consisting of chewy based lozenge, hard based lozenge, caramel based lozenge, pastilles, troches, soft lozenge, center filled lozenge, liquid filled lozenge, power based lozenge, compressed lozenge, syrup based lozenge, granulated lozenge, buccal tablet and sublingual tablet.

4. The composition of claim 1, wherein the oral dosage form is selected from a group consisting of a bi-layer tablet, layer tablet and multi-layer tablet.

5. The composition of claim 1, wherein the composition further comprises a pharmaceutically acceptable excipient.

6. The composition of claim 5, wherein the pharmaceutically acceptable excipient is selected from any or a combination of: a diluent, an anti-oxidant, a preservative, an alkalizing agent, a buffering agent, a disintegrant, a binder, an anti-foaming agent, a solvent, a glidant, a lubricant, a flavoring agent, a sweetener, a coating agent, a rate controlling polymer or non-polymer, a zinc salt, a fatty acid, an amino acid, amino acid metabolites, a bulking agent, an anti-tacking agent, an emulsifier, a surfactant, a plasticizer and a stabilizer.

7. The composition of claim 6, wherein the fatty acid further comprises any or a combination of diglyceryl lauryl fumarate, diglyceryl lauryl succinate, and diglyceryl capryl succinate.

8. The composition of claim 1, wherein the composition comprises an intra-granular portion and an extra-granular portion, wherein the intra-granular portion comprises Famotidine or salt thereof, Lidocaine or salt thereof, Melatonin or salt or thereof and a pharmaceutically acceptable excipient, and the extra-granular portion comprises a pharmaceutically acceptable excipient.

9. The composition of claim 1, wherein the composition comprises an intra-granular portion and an extra-granular portion, wherein the intra-granular portion comprises Lidocaine or salt thereof, Melatonin or salt thereof and a pharmaceutically acceptable excipient, and the extra-granular portion comprises Famotidine or salt thereof and a pharmaceutically acceptable excipient.

10. The composition of claim 1, wherein the composition comprises an intra-granular portion and an extra-granular portion, wherein the intra-granular portion comprises the Famotidine or salt thereof, the Melatonin or salt thereof, and a pharmaceutically acceptable excipient, and the extra-granular portion comprises the Lidocaine or salt thereof and a pharmaceutically acceptable excipient.

11. The composition of claim 1, wherein the composition comprises an intra-granular portion and an extra-granular portion, wherein the intra-granular portion comprises Famotidine or salt thereof and Lidocaine or salt thereof and a pharmaceutically acceptable excipient, and the extra-granular portion comprises Melatonin or salt thereof and a pharmaceutically acceptable excipient.

12. The composition of claim 1, wherein the composition comprises an intra-granular portion and an extra-granular portion, and wherein the portions are compressed together to obtain any of a tablet dosage form and a Lozenge dosage form, optionally coated with a seal coat.

13. The composition of claim 1, wherein the composition comprises an intra-granular portion and an extra-granular portion, and wherein the intra-granular portion comprises Famotidine in an amount of 40 mg, Lidocaine hydrochloride monohydrate in an amount of 100 mg, Melatonin in an amount of 10 mg, and a pharmaceutically acceptable excipient, and the extra-granular portion comprises a pharmaceutically acceptable excipient.

14. A method of treating oral and gastrointestinal disorders in a patient in need thereof comprising administering to the patient a therapeutically effective amount of a pharmaceutical composition of claim 1.

\* \* \* \* \*